| United States Patent | (10) Patent No.: US 9,314,643 B2 |
| Kucher et al. | (45) Date of Patent: Apr. 19, 2016 |

(54) HEART THERAPY DEVICE FOR DETECTING VENTRICULAR TACHYCARDIA AND FIBRILLATION

(71) Applicant: BIOTRONIK SE & CO. KG, Berlin (DE)

(72) Inventors: Andreas Kucher, Schwedt (DE); Thomas Doerr, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 27 days.

(21) Appl. No.: 14/324,015

(22) Filed: Jul. 3, 2014

(65) Prior Publication Data

US 2015/0025593 A1 Jan. 22, 2015

Related U.S. Application Data

(60) Provisional application No. 61/847,093, filed on Jul. 17, 2013, provisional application No. 61/865,625, filed on Aug. 14, 2013.

(51) Int. Cl.
| *A61N 1/39* | (2006.01) |
| *A61N 1/362* | (2006.01) |
| *A61N 1/365* | (2006.01) |
| *A61N 1/368* | (2006.01) |
| *A61N 1/37* | (2006.01) |

(52) U.S. Cl.
CPC ............ *A61N 1/3987* (2013.01); *A61N 1/3622* (2013.01); *A61N 1/3684* (2013.01); *A61N 1/36592* (2013.01); *A61N 1/37* (2013.01); *A61N 1/3962* (2013.01)

(58) Field of Classification Search
CPC .... A61N 1/362; A61N 1/3962; A61N 1/3622
USPC .................................. 607/4, 5, 14
See application file for complete search history.

(56) References Cited

U.S. PATENT DOCUMENTS

| 2006/0116747 A1* | 6/2006 | Eick ........................ A61N 1/056 607/122 |
| 2007/0255327 A1 | 11/2007 | Cho et al. |
| 2009/0125077 A1 | 5/2009 | Doerr et al. |
| 2009/0306731 A1* | 12/2009 | Doerr ................... A61N 1/3692 607/5 |
| 2011/0082512 A1 | 4/2011 | Doerr |
| 2013/0030314 A1 | 1/2013 | Keel et al. |

OTHER PUBLICATIONS

European Search Report received for EP Appl. No. 14168458.9 dated Jul. 18, 2014, 4 pages.

* cited by examiner

*Primary Examiner* — Theodore Stigell
*Assistant Examiner* — Roland Dinga
(74) *Attorney, Agent, or Firm* — Arc IP Law, PC; Joseph J. Mayo

(57) ABSTRACT

A heart therapy device having a right-ventricular electrode and a left-ventricular electrode connected to a tachycardia identification unit. The tachycardia identification unit identifies ventricular tachycardia and simultaneously evaluates the heart rate at the right-ventricular and left-ventricular electrodes. The ventricular electrodes each include an electrode line having a corresponding sensing electrode pole that senses electric potential courses in the myocardium of the respective ventricle. The heart therapy device includes a dislocation identification unit that detects a possible dislocation of one of the ventricular electrodes, simultaneously evaluates the heart rate at both ventricular electrodes, and signals a right-ventricular or left-ventricular dislocation when a sudden rise in heart rate is sensed at the right-ventricular or left-ventricular electrode, without detecting a considerable change in rhythm at the respective electrode. In the event of the dislocation of one of the ventricular electrodes, the rhythm information of the electrode in question is ignored for tachycardia detection.

15 Claims, 7 Drawing Sheets

HEART THERAPY DEVICE FOR DETECTING VENTRICULAR TACHYCARDIA AND FIBRILLATION

This application claims the benefit of U.S. Provisional Patent Application 61/847,093, filed on 17 Jul. 2013, and U.S. Provisional Patent Application 61/865,625, filed on 14 Aug. 2013, the specifications of which are hereby incorporated herein by reference.

BACKGROUND OF THE INVENTION

1. Field of the Invention

Embodiments of the invention generally relate to implantable biventricular heart therapy devices that detect ventricular tachycardia and fibrillation.

2. Description of the Related Art

Typically, tachycardia identification units allow biventricular detection of tachyarrhythmias, such as ventricular tachycardias (VT) or fibrillations (VF). Generally, therapy device control may initiate suitable therapies based on the detection.

A system known as an S-ICD system typically operates with a far-field channel for VT/VF identification.

For example, a specific type of tachyarrhythmias is "dissimilar" ventricular tachycardias, in which different (beat or contraction) rates prevail in the right ventricle (RV) and in the left ventricle (LV).

Generally, ICD systems available on the market operate exclusively with a right-ventricular VT/VF identification channel. The left-ventricular sensing signals are typically used only for the inhibition of unnecessary LV stimulation and for the recording of an intracardial electrocardiogram (IEGM), but not for VT/VF identification. Based on the observation that there are ventricular tachycardias that have a considerable frequency difference between the right and left ventricle over a considerable period of time, typically, in the event of just right-ventricular detection, there is a potential risk that patients having these dysrhythmias are not being cared for sufficiently.

For example, with a much quicker VT/VF in the left ventricle with a moderate VT in the right ventricle, generally, there is a risk of a lethal appearance of the dysrhythmia, since the time it takes for effective defibrillation is considerably too long as a result of the underestimation only using right-ventricular sensing.

Typically, purely biventricular sensing poses a risk that, for example in the event of a left-ventricular electrode (coronary sinus electrode) dislocated in the region of the atrium, an atrial fibrillation is incorrectly classified as left-ventricular fibrillation (left-VF) and thus leads to an inadequate therapy delivery. A dislocated right-ventricular electrode, generally, may cause a comparable effect.

As such, typically, isolated left-ventricular tachyarrhythmias may be cited as particularly relevant, since they are not generally correctly detected and treated using existing right-ventricular systems. Analyses of biventricular IEGM recordings, generally, reveal a considerable proportion of dysrhythmias of this type.

Known biventricular heart therapy devices are generally inadequate with respect to dissimilar ventricular tachycardias. In view of the above, there is a need for a biventricular heart therapy device, which is able to adequately respond to dissimilar ventricular tachycardias.

BRIEF SUMMARY OF THE INVENTION

One or more embodiments of the invention are related to an implantable biventricular heart therapy device having a therapy device control unit, which includes a tachycardia identification unit connected, at least indirectly, to a right-ventricular sensing electrode and a left-ventricular sensing electrode. In at least one embodiment of the invention, the right-ventricular sensing electrode and the left-ventricular sensing electrode feed at least one signal from the heart's right ventricle and at least one signal from the heart's left ventricle, respectively to the tachycardia identification unit. In one or more embodiments, the signals represent a course over time of electrical potentials in the heart. During operation, in one or more embodiments, the signals representing a course over time of electric potentials in the heart or signals derived therefrom are fed to the tachycardia identification unit. By way of at least one embodiment, the tachycardia identification unit may evaluate the signals fed thereto or the course over time thereof, and generate a tachyarrhythmia signal if the fed signal meets predefined criteria, for example frequency criteria with regard to specific signal features, such as detected R waves. Due to the output of a tachyarrhythmia signal, in one or more embodiments, the tachycardia identification unit may signal a (pathological) tachycardia or fibrillation. In at least one embodiment, the heart therapy device may include an implantable cardioverter-defibrillator (ICD). Embodiments of the invention are generally configured to respond adequately to dissimilar ventricular tachycardias.

In one or more embodiments, the tachycardia identification unit may simultaneously evaluate the heart rate at the right-ventricular and at the left-ventricular sensing electrode to identify ventricular tachycardia.

In at least one embodiment, the therapy device control may include a dislocation identification unit connected, at least indirectly, to the right-ventricular sensing electrode and the left-ventricular sensing electrode. As such, in one or more embodiments, during operation, the signals representing a course over time of electric potentials in the heart or signals derived therefrom are fed to the dislocation identification unit. In at least one embodiment, the dislocation identification unit may simultaneously evaluate the heart rate at the right-ventricular and the left-ventricular sensing electrodes, signal a right-ventricular or left-ventricular dislocation, and generate a corresponding dislocation signal whenever the dislocation identification unit senses a sudden rise in heart rate at the right-ventricular or left-ventricular electrode, without detecting a significant rhythm change at the left-ventricular or the right-ventricular electrode within a predefined and/or adjustable time window. In one or more embodiments the therapy device control unit, in the event of a signaled dislocation of the right-ventricular or the left-ventricular electrode, may ignore the rhythm information of the dislocated right-ventricular or left-ventricular sensing electrode, or electrode in question, during tachycardia detection.

The left-ventricular and/or right-ventricular signals fed into the tachycardia identification unit and to the dislocation identification unit, in at least one embodiment of the invention, may be signals derived from the signals sensed by the respective electrodes, for example marker signals generated by corresponding right-ventricular/left-ventricular sensing units, when one or more of the right-ventricular sensing unit, the left-ventricular sensing unit, the right-ventricular sensing electrode and the left-ventricular sensing electrode detect right-ventricular or a left-ventricular chamber contraction, for example on the basis of a corresponding R-spike in the electrocardiogram.

The heart therapy device, according to one or more embodiments the invention, ensures an adequate antitachycardia therapy for ICD patients, in which dissimilar ventricular VT/VF episodes occur, for example tachycardia dysrhythmias, that may progress at different speeds in the right ventricle and in the left ventricle. The heart therapy device, according to at least one embodiment the invention, may prevent an atrial fibrillation from accidentally being incorporated into the VT/VF detection via a dislocated ventricle electrode.

One or more embodiments of the invention allow an adequate therapy in good time in patients having ventricular tachycardias of different speeds in both ventricles, without an inadequate therapy being delivered in the event of an electrode dislocation. In at least one embodiment, the heart therapy device enables the avoidance of incorrect detections in the event of a dislocated probe, or electrode, and simultaneous atrial fibrillation.

During operation, the heart therapy device according to at least one embodiment of the invention, may include an implantable defibrillator having at least one right-ventricular electrode and at least one left-ventricular (preferably coronary sinus) electrode, wherein each electrode may be connected to a tachycardia identification unit. In one or more embodiments, the tachycardia identification unit may, to identify ventricular tachycardias, simultaneously evaluate the heart rate at the right-ventricular and at the left-ventricular electrode. In at least one embodiment, the right-ventricular and left-ventricular electrode, in each case, correspond to a sensing electrode pole for bipolar or unipolar sensing of electric potential courses in the myocardium of the respective ventricle. In one or more embodiments, the electrode poles, for example, may be part of a corresponding electrode line and may be connected via the electrode line to the heart therapy device. According to at least one embodiment, the dislocation identification unit allows the detection of a possible dislocation of one of the ventricular electrodes and may simultaneously evaluate the heart rate at the right-ventricular and the left-ventricular electrode. In one or more embodiments, the dislocation identification unit may signal a right-ventricular or left-ventricular dislocation whenever a sudden rise in heart rate is sensed at the right-ventricular or left-ventricular electrode, without detecting a considerable change in rhythm at the left-ventricular or right-ventricular electrode around the same time, such that, in the event of a signaled dislocation of one of the ventricular electrodes, the rhythm information of the dislocated electrode, or electrode in question, may be ignored for, or during, tachycardia detection.

In one or more embodiments, the tachycardia identification unit, following a dislocation signal of the dislocation identification unit, may ignore a signal originating from a respective dislocated electrode, or electrode in question, for, or during, the tachycardia detection. In at least one embodiment, the signal originating from an electrode identified as being dislocated, may not be fed to the tachycardia identification unit.

One or more embodiments of the invention include at least one atrial electrode, wherein the heart therapy device may only carry out the electrode dislocation check using the dislocation identification unit when an atrial fibrillation (AF) is sensed at the at least one atrial electrode. For example, in at least one embodiment, an AF identification unit that detects atrial fibrillations may be provided. In one or more embodiments, in the event of a detected atrial fibrillation, the AF identification unit may output an AF signal that may cause a deactivation of the dislocation identification unit.

By way of at least one embodiment, the dislocation identification unit may use at least one criteria of the following criteria or a combination thereof, to identify, or signal, the left-ventricular dislocation identification: a maximum permissible anteriority of a left-ventricular contraction before a right-ventricular contraction, stability of A-RV conductor time (conductor time from the atrium to the right ventricle), a rate comparison between the atrium and heart's left ventricle, a left-ventricular stimulation stimulus threshold, and morphology of left-ventricular R-waves before a preliminarily detected tachycardia with confirmed amplitudes impedances and stimulus thresholds.

According to at least one embodiment, the heart therapy device may include a three-chamber device and a right-atrial electrode wherein the three-chamber device is connected to the right-atrial electrode, the right-ventricular electrode and the left-ventricular electrode. The tachycardia identification unit, in at least one embodiment, may perform a three-chamber discrimination algorithm, which is extended by comparison, in which, to classify the origin of a tachycardia, interval information of the left ventricle is and A-LV conductor times from the atrium to the left ventricle are recorded.

By way of one or more embodiments, to discriminate between a physiological rise in heart rate (which leads to a sinus tachycardia) and a ventricular tachycardia of sudden onset, the tachycardia identification unit may extend an onset criterion (such as a sudden onset or a sudden rise in the heart rate within one heart cycle or just a rather low number of heart cycles) by the left-ventricular rhythm evaluation, and may signal a sinus tachycardia (by outputting a corresponding tachyarrhythmia signal) whenever there is no sudden rise in heart rate in the right ventricle and no sudden rise in heart rate in the left ventricle, and/or the interventricular conductor times (the A-LV conductor times and the A-RV conductor times) remain unchanged under consideration of a tolerance.

In at least one embodiment, the tachycardia identification unit may apply a ventricular stability criterion to distinguish between a stable monomorphic ventricular tachycardia and a conducted atrial fibrillation in extended form, wherein a ventricular tachycardia (VT) is then only detected when the rhythm in both ventricles is classified as stable.

The heart therapy device, in at least one embodiment, includes a therapy control, such that the heart therapy device may automatically switch the timer control over to the left-ventricular side (such that the times are controlled based on detected left-ventricular events) using the therapy device control unit. In one or more embodiment, using the timer control, the heart therapy device may control blank-out times necessary for the tachycardia detection, the left-ventricular signals are classified as suitable for the tachycardia detection, for example when no dislocation is identified. United Stated Patent Publication 2011/0082512 and European Patent 2 308 558, both of which are incorporated herein by reference, relating to a cardiac stimulator that may detect a stability parameter, include a timer control and a programmable automatic switch applicable to the present invention. Blank-out time, that is to say periods in which a respective sensing unit either cannot sense cardiac events or periods in which sensed cardiac events, in at least one embodiment, are ignored for the tachycardia identification.

According to at least one embodiment, the tachycardia identification unit for the biventricular detection may include two separate detection counters for the right-ventricular and the left-ventricular signal, such as a right ventricle detection counter and a left ventricle detection counter. In at least one embodiment, when a predefined counter state is reached, one of the two counters, the right ventricle detection counter and the left ventricle detection counter triggers a corresponding detection and therefore a corresponding tachyarrhythmia signal.

In one or more embodiments, the tachycardia identification unit for biventricular detection may include at least one single common detection counter for both the at least one right-ventricular signal and the at least one left-ventricular signal, wherein, in the event of, or during, a deviating interval time between the at least one right-ventricular signal and at least one the left-ventricular signal, tachycardia detection is always determined by the quicker ventricle, via the at least one single common detection counter.

Regarding a termination criterion, used for the therapy device control unit to terminate an antitachycardia therapy (ATP, antitachycardia pacing), by way of at least one embodiment, the therapy device control unit may implement a termination criterion, which is then only considered to be met when measured interval times in both the right ventricle and in the left ventricle are greater than a predefined interval limit for the termination.

In one or more embodiments, the therapy device control unit may consider the termination criterion to be met when the measured interval time, only in the right ventricle, is greater than a predefined interval limit for the termination.

According to at least one embodiment, the heart therapy device may include a right-ventricular and left-ventricular undersense identification, for example, using a plausibility check of numbers of one or more of right-ventricular and left-ventricular intervals and atrial intervals. In one or more embodiments, the heart therapy device may switch over to a right-ventricular or left-ventricular detection whenever one of the ventricular electrodes has considerable undersensing, for example when one of the ventricular electrodes detects much fewer cardiac cycles than the other electrode(s), due in part to undetected cardiac events.

In at least one embodiment, the tachycardia identification unit may be switched between a purely, or exclusively, right-ventricular tachycardia identification, in which only signals originating from a right-ventricular electrode and possibly additionally from an atrial electrode are evaluated for the tachycardia identification, and a biventricular tachycardia identification, in which signals also originating from a left-ventricular electrode are evaluated for the tachycardia identification. After implantation of the heart therapy device or a connected electrode line, in at least one embodiment, a purely, or exclusively, right-ventricular detection may thus always initially occur, until a stable electrode position in the left ventricle has been automatically determined by the heart therapy device, and the biventricular detection is then automatically activated. In at least one embodiment, the heart therapy device enables and may carry out automatic switchover between different tachycardia identification techniques.

In at least one embodiment, one or more of the heart therapy device may include a shock electrode that delivers at least one defibrillation shock, wherein the heart therapy device and/or the therapy control unit may carry out an additional dislocation check of the left-ventricular sensing electrode as discussed above, or after each delivery of the at least one defibrillation shock.

According to at least one embodiment, the dislocation identification unit may only detect a dislocation of a left-ventricular electrode, wherein the dislocation identification carried out by the dislocation identification unit relates only to a respective left-ventricular (coronary sinus) electrode, wherein the likelihood of a dislocation is greater.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
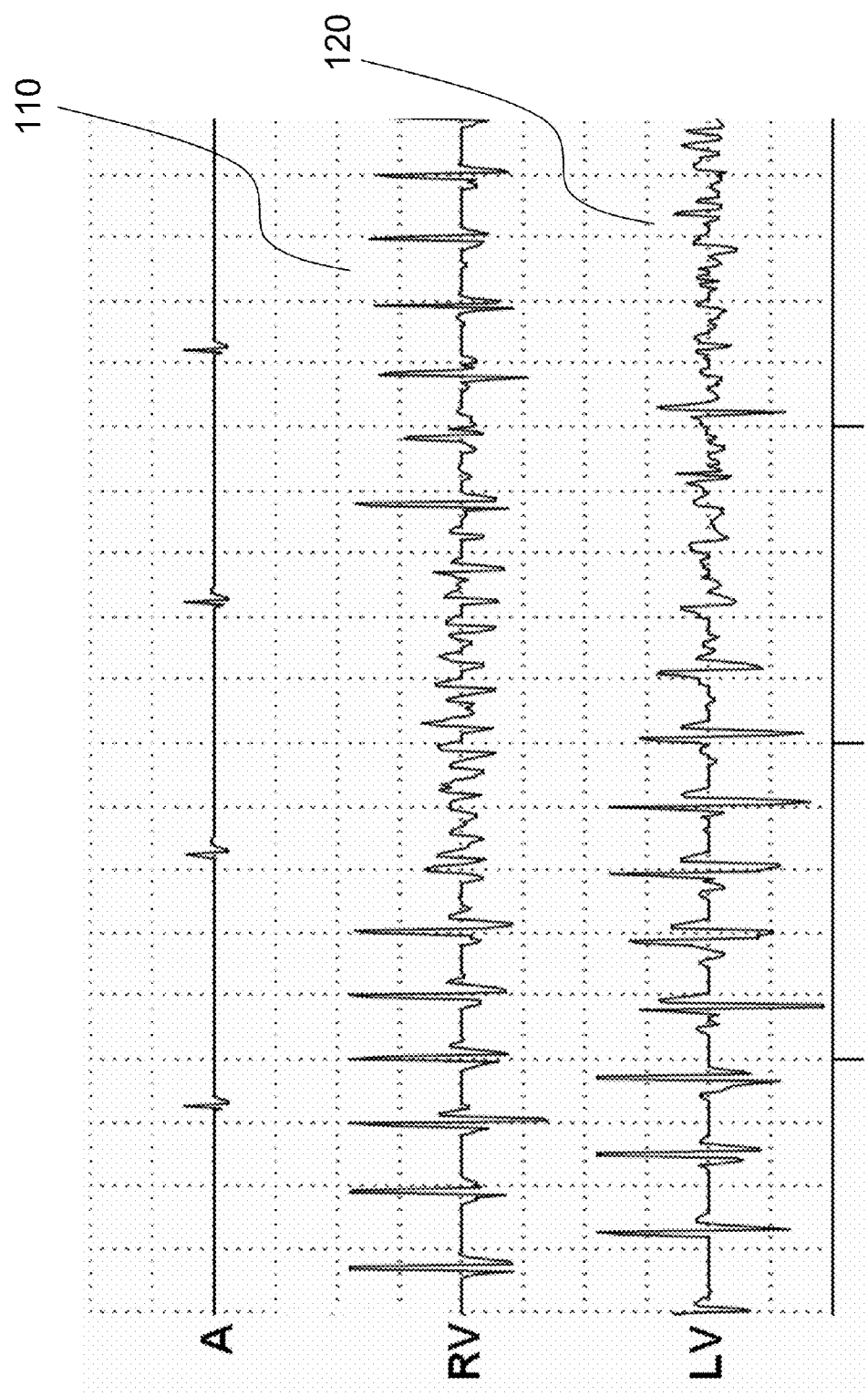
FIG. 1: shows an example of a dissimilar ventricular tachyarrhythmia.

FIG. 1 shows an example of a dissimilar ventricular tachyarrhythmia. As shown in FIG. 1, the rhythm changes in the right ventricle (RV) from a stable VT over a short phase of VF to a slower VT 110, and at the same time the rhythm in the LV channel changes at a later moment in time from a stable VT to a lasting VF, which is not sensed with a purely right-ventricular detection and may lead to an incorrect choice of therapy.

Figure 2:
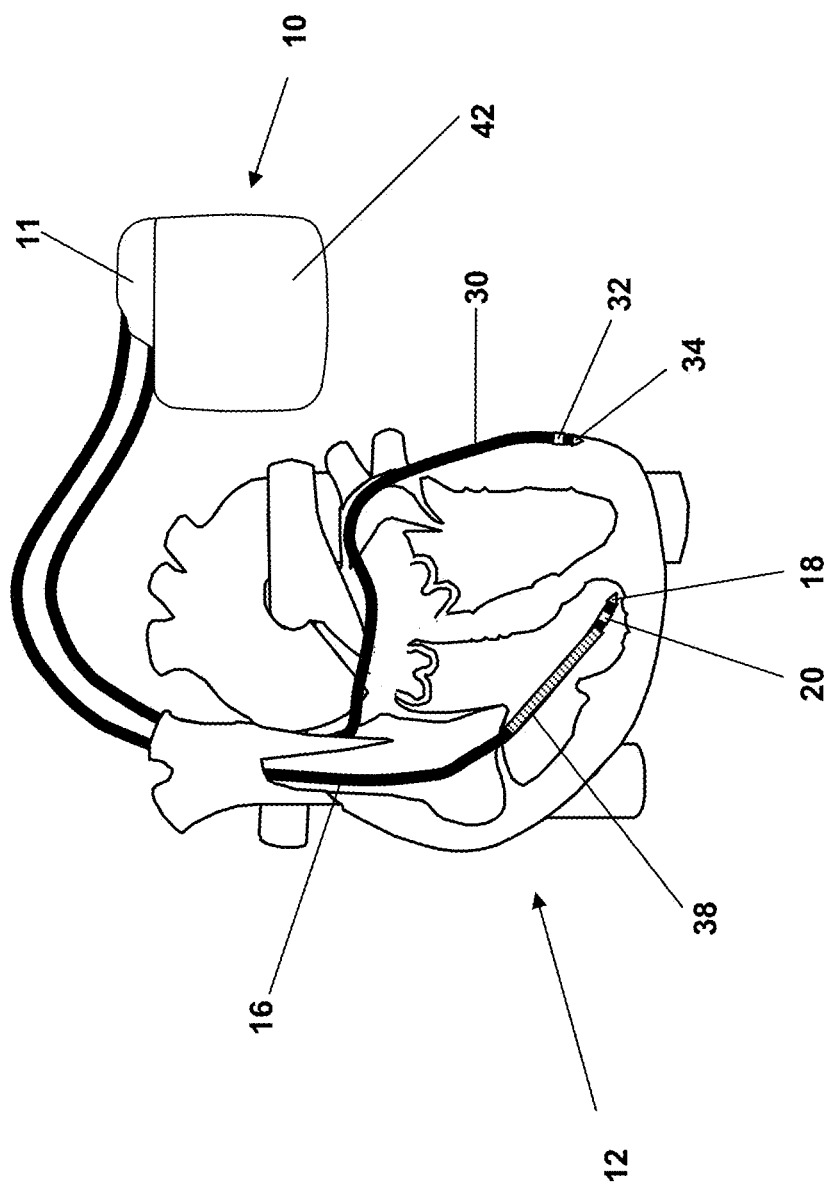
FIG. 2: shows a biventricular cardiac pacemaker, with a right-ventricular defibrillation shock coil, as an implantable cardiac stimulator.

FIG. 2 shows a biventricular cardiac pacemaker-defibrillator (ICD or CRT-D), having a right-ventricular defibrillation shock coil, as an implantable cardiac stimulation such as an implantable heart therapy device (heart stimulator) 10, according to at least one embodiment of the invention. In at least one embodiment, the implantable heart therapy device 10 is connected via electrode lines 16 and 30 to stimulation electrodes 18 and 20, and to sensing electrodes 32 and 34, in the right and left ventricle of a heart respectively. In one or more embodiments, the heart therapy device may deliver stimulation pulses to the heart and record electric potentials from the heart.

The electrode lines 16 and 30, in at least one embodiment, are electrically connected via plug connections to contact sockets in a header (terminal housing) 11 of the heart stimulator 10. In one or more embodiments, the electrode lines 16 and 30 may be connected to electronic components inside a hermetically tight metal housing 42 of the heart stimulator 10. The electronic components, according to at least one embodiment, schematically illustrated hereinafter in FIG. 3, may determine the operating principles of the heart stimulator 10.

In one or more embodiments, the electrode line 16 is a right-ventricular electrode line and has at its distal end a right-ventricular tip electrode pole RV Tip 18, and in a direct or indirect vicinity thereof a right-ventricular ring electrode pole RV Ring 20. In at least one embodiment, both electrode poles may be arranged in the apex of the right ventricle of the heart 12.

According to at least one embodiment, the electrode line 30 is a left-ventricular electrode line and includes at the distal end a bipolar stimulation and sensing electrode having a distal tip electrode pole LV Tip 34, and in the direct or indirect vicinity thereof a left-ventricular ring electrode pole LV Ring 32. In one or more embodiments, the left-ventricular electrode line 30 may be guided from the right atrium 26 of the heart 12 (illustrated in FIG. 4) via the coronary sinus into a lateral vein branching therefrom, also referred to as the coronary sinus electrode line or CS electrode line.

In at least one embodiment, the right-ventricular electrode line 16 may include a right-ventricular shock coil RV Shock 38, such as a large-area electrode pole that delivers defibrillation shocks.

Figure 3:
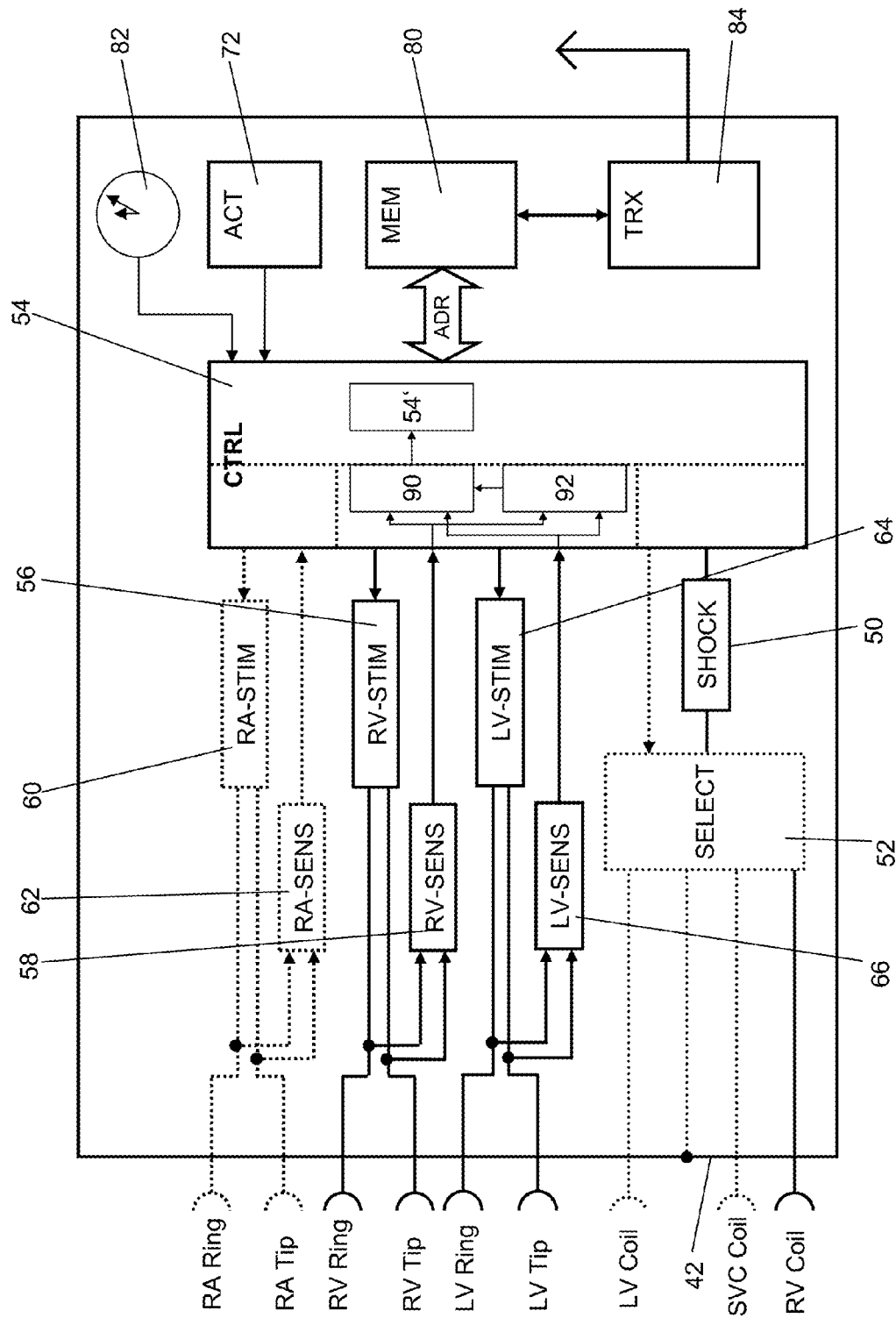
FIG. 3: shows components of the implantable cardiac stimulator of FIG. 2 in the form of a simplified block diagram.

FIG. 3 shows components, such as key functional units, of the heart stimulator 10. Also in FIG. 3, additional components are illustrated via dashed lines, as may be provided in at least one embodiment of the invention.

By way of one or more embodiments, as shown on the left hand side, electrical terminals for the various electrode poles 18, 20, 32, 34 and 38 are illustrated. The shock electrode (shock coil) 38, in at least one embodiment, is connected to a shock pulse generator 50. In one or more embodiments, the shock pulse generator 50 may be connected to a control unit 54, which controls the shock pulse generator 50, as required, to generate and deliver a cardioversion or defibrillation shock. In at least one embodiment, the control unit 54 acts as a therapy device control unit 54'. The therapy device control unit 54', in at least one embodiment of the invention, may be connected, for example, to the shock pulse generator 50, to a right-ventricular stimulation unit 56, and to a left-ventricular stimulation unit 64.

The control unit 54, in at least one embodiment, may include a tachycardia identification unit 90 and a dislocation identification unit 92.

By way of one or more embodiments, the terminal for the right-ventricular tip electrode pole RV Tip, and the terminal for the right-ventricular ring electrode pole RV Ring, are each connected to both the right-ventricular stimulation unit 56 and to a right-ventricular sensing unit 58. Both the right-ventricular stimulation unit 56 and the right-ventricular sensing unit 58, in one or more embodiments, are each connected to the control unit 54.

According to at least one embodiment, the right-ventricular stimulation unit 56, following a control signal of the control unit 54, may generate a right-ventricular stimulation pulse and may deliver the right-ventricular stimulation pulse via the terminals for the right-ventricular ring electrode pole and the right-ventricular tip electrode pole. In one or more embodiments, the housing 42 of the heart stimulator 10 may form a neutral electrode, and the right-ventricular stimulation unit 56 may be connected to the terminal for the right-ventricular tip electrode pole RV Tip and to the housing 42 as another electrode to deliver a stimulation pulse. In at least one embodiment, a right-ventricular stimulation pulse differs from a defibrillation shock in that the stimulation pulse has a much lower pulse intensity, such that, by contrast to a defibrillation shock, it does not excite the entire heart tissue (myocardium) of an atrium in one attempt, but only the heart muscle cells in the direct vicinity of the right-ventricular tip electrode pole 18. In one or more embodiments, the excitation then propagates further as a result of natural conduction over the entire ventricle and thus ensures a stimulated contraction of the ventricle.

In at least one embodiment, the right-ventricular sensing unit 58 may first amplify, using an input amplifier, and then filter electric potentials applied across the terminal for the right-ventricular ring electrode pole RV Ring and the right-ventricular tip electrode pole RV Tip. By way of one or more embodiments, the right-ventricular sensing unit 58 may evaluate the course of the electric signals applied across its inputs in such a way that the right-ventricular sensing unit 58 automatically detects a natural (intrinsic) beat, such as an automatic contraction of the right ventricle. In at least one embodiment, the evaluation may be achieved, for example, by comparing the course of the signal applied across the inputs of the right-ventricular sensing unit 58 to a threshold value. In one or more embodiments, the largest amplitude of the signal is in the form of an R-spike, which is characteristic for a natural contraction of the right ventricle and which may be detected by comparison with a threshold value. In at least one embodiment, the right-ventricular sensing unit 58, therefrom, may output a corresponding output signal (for example a marker signal), indicating a natural contraction of the right ventricle, to the control unit 54, the tachycardia identification unit 90 and the dislocation identification unit 92 thereof.

In one or more embodiments, the terminal for the left-ventricular tip electrode pole LV Tip and the terminal for the left-ventricular ring electrode pole LV Ring are also connected to the left-ventricular stimulation unit 64 and a left-ventricular sensing unit 66. In at least one embodiment, the left-ventricular stimulation unit 64 and the left-ventricular sensing unit 66 may be connected to the control unit 54. In one or more embodiments, the left-ventricular stimulation unit 64 and the left-ventricular sensing unit 66 may function similarly to the stimulation units 56 and 60 and sensing units 58 and 62 as described above.

In at least one embodiment, the heart stimulator 10 may include an activity sensor 72 connected to the control unit 54. The activity sensor 72, in one or more embodiments, may detect a signal, for example a motion signal, dependent on the physical activity of a patient and may output a corresponding signal to the control unit 54 indicating the physical activity of the patient. As such, in at least one embodiment, the control unit 54 may adapt the timing of the stimulation pulse to the demand of the patient (haemodynamic demand).

According to at least one embodiment, the heart stimulator 10 may include a memory unit 80, connected to the control unit 54, that stores signals generated or evaluated by the control unit 54. In one or more embodiments, the memory unit 80 may store control programs for the control unit 54 in modifiable form. In at least one embodiment, the control unit 54 may be connected to a timer 82.

By way of one or more embodiments, the heart stimulator 10 may include at least one bidirectional telemetry interface 84 to transfer stored data from the implant 10 to an external device 100 and, vice versa, to also receive program settings and therapy commands from the external device 100.

Figure 4:
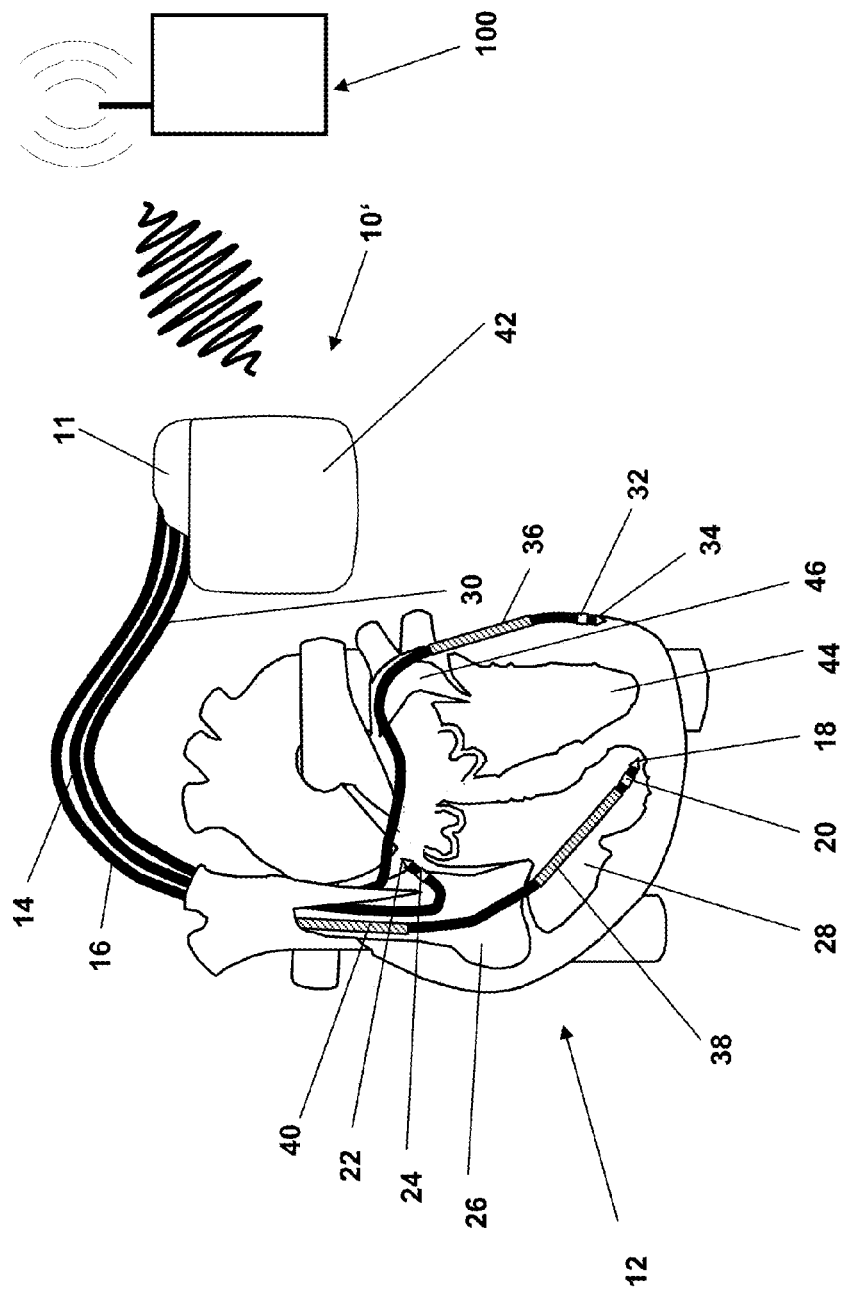
FIG. 4: shows a biventricular three-chamber cardiac pacemaker and implantable cardioverter-defibrillator (ICD) as an implantable cardiac stimulator.

FIG. 4 shows a biventricular three-chamber cardiac pacemaker and implantable cardioverter-defibrillator (ICD) as an implantable cardiac stimulator. As shown in FIG. 4, the implantable cardiac stimulator 10', in at least one embodiment, is connected via its terminal block 11 (header) to one or more of a right-ventricular electrode line 16, a left-ventricular electrode line 30 and a right-atrial electrode line 14.

In one or more embodiments, the electrode lines may be implanted permanently in the heart 12. In at least one embodiment, the right-ventricular electrode line 16 has at the distal end a bipolar stimulation and sensing electrode with a tip electrode pole RV Tip 18 and ring electrode pole RV Ring 20. According to at least one embodiment, the electrode line may include a distal shock coil RV Coil 38 and additionally a proximal shock coil SVC Coil 40. The distal shock coil RV Coil 38, in at least one embodiment, may be arranged such that it is located in the right ventricle 28. The proximal shock coil SVC Coil 40, in at least one embodiment, may be located in the upper part of the right atrium 26 or in the superior vena cava (precava).

By way of one or more embodiments, the electrode line 14 is an atrial electrode line and may include at the distal end a bipolar stimulation and sensing electrode, formed by a tip electrode pole RA Tip 22 and a ring electrode pole RA Ring 24, implanted in the right atrium 26.

As shown in FIG. 4, according to one or more embodiments, the left-ventricular electrode line 30 may include a left-ventricular shock coil 36 to deliver defibrillation shocks to the left ventricle. In at least one embodiment, the shock coil 36 may reach out from the left ventricle 44 as far as the left atrium 46. In at least one embodiment, the implantable cardiac stimulator 10' may include a second electrode, to deliver a shock, as the electrically active housing 42 of the implant 10'.

As shown from FIG. 3, in at least one embodiment of the invention, according to the components illustrated in a dotted manner, the terminal for the right-atrial tip electrode pole and the terminal for the right-atrial ring electrode pole may be connected to both a right-atrial stimulation unit 60 and to a right-atrial sensing unit 62, which are each in turn connected to the control unit 54. In one or more embodiments, the right-atrial stimulation unit 60 may generate stimulation pulses, of which the intensity is sufficient to excite the right-atrial myocardium. In at least one embodiment, the right-atrial stimulation pulses may have a pulse intensity different from the right-ventricular stimulation pulses. The right-atrial sensing unit 62, in at least one embodiment, may detect a P-wave from the course of the differential signal applied across the inputs thereof, wherein the P-wave represents a natural (intrinsic) contraction of the right atrium. If the right-atrial sensing unit 62 detects a corresponding P-wave, in at least one embodiment of the invention, it generates an output signal and forwards the output signal to the control unit 54, wherein the output signal represents a natural contraction of the right atrium.

As shown in FIG. 3, according to the components shown in a dotted manner, the left-ventricular shock coil 36, as illustrated in FIG. 4, may be connected to the shock generator 50 via a terminal LV-COIL and an electrode selection unit 52. Using the electrode selection unit 52, in one or more embodiments, the control unit 54 may select two or more electrodes (including the conductive housing 42), via which a shock is delivered.

According to the heart therapy devices illustrated in FIGS. 2 to 4, according to at least one embodiment of the invention, the tachycardic ventricular dysrhythmias may be classified simultaneously by the right-ventricular and the left-ventricular electrode line, primarily via the sensed heartbeats, wherein the quicker dysrhythmia primarily determines the therapy selection. At the same time, in at least one embodiment, a check is also performed for a possible dislocation of one of the ventricular electrodes in order to prevent inadequate therapy delivery. If such a dislocation is determined, in one or more embodiments, the relevant, dislocated or possibly dislocated, electrode is no longer used for the tachycardia detection.

Figure 5:
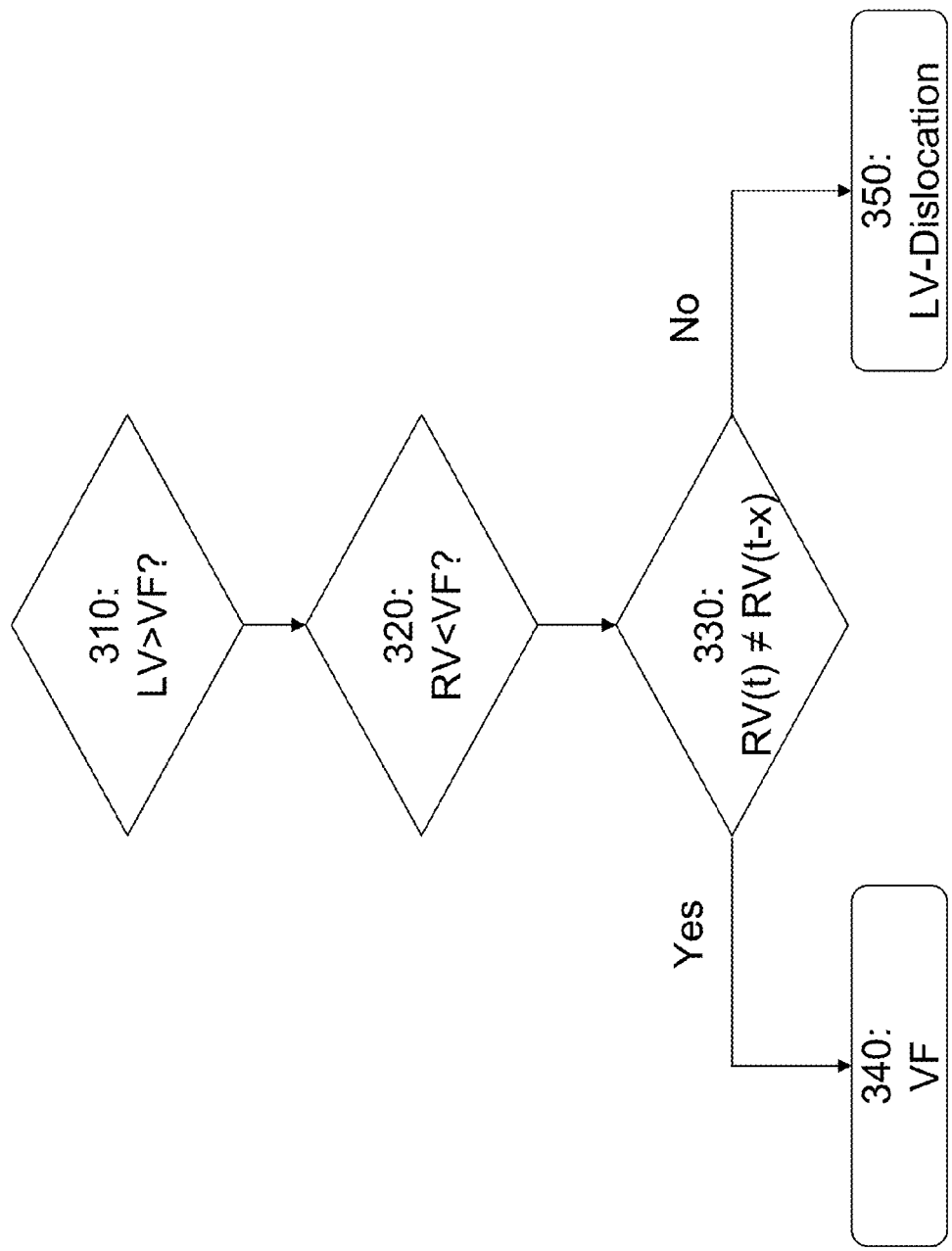
FIG. 5: shows a flow diagram illustrating the dislocation identification.

FIG. 5 shows a flow diagram illustrating the dislocation identification. In at least one embodiment, the dislocation identification is provided for the biventricular detection and may be carried out by the dislocation identification unit 92. FIG. 5 shows an example of an LV dislocation identification, that is to say an identification of a dislocation of the left-ventricular electrode, according to at least one embodiment of the invention.

Figure 6:
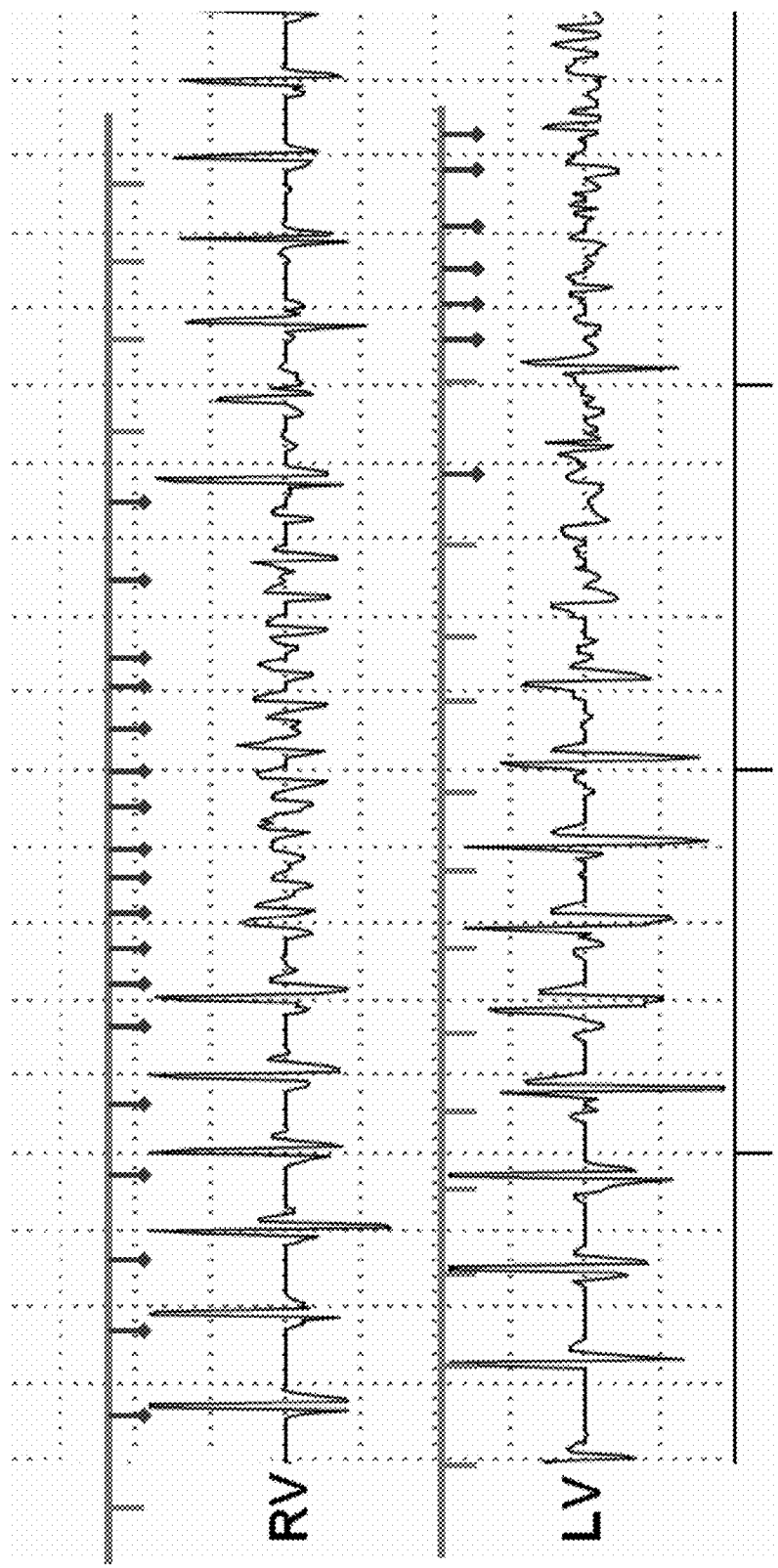
FIG. 6: shows an example of biventricular detection.

Since the left-ventricular electrode line 30 (and therefore the left-ventricular electrode that surrounds the left-ventricular tip electrode pole LV Tip 34 and the left-ventricular ring electrode pole LV Ring 32), in one or more embodiments, may shift within the coronary vein in such a way that the electrode poles 32 and 34 are therefore located in the region of the atrium, it is not ruled out that an atrial tachycardia is incorrectly sensed as a left-ventricular tachycardia, and an inadequate therapy is initiated with biventricular detection (as described further below with reference to FIG. 6).

In at least one embodiment, the dislocation identification unit 92 checks a possible dislocation of the left-ventricular electrode as follows:

If the left-ventricular rate lies in a range of a VT/VF zone 310, and if the right-ventricular rate lies in no zone or in a slower zone 320, in one or more embodiments, the right-ventricular rate is checked as to whether it has changed significantly at the start of a respective left-ventricular tachycardia 330. In at least one embodiment, if the right-ventricular rate remains largely unchanged, the heat therapy device thus detects a dislocation of the left-ventricular electrode 350, and otherwise an actual ventricular arrhythmia 340.

According to at least one embodiment, to further improve the specificity of the dislocation identification, further electrodes and ECG discharge lines, such as a right-atrial electrode or a far-field ECG, may be used. In one or more embodiments, the criteria for LV dislocation identification may additionally include one or more of the following information for example:

maximum anteriority of an LV sense before RV sense;
stability check of the A-RV conductor time;
comparison of the atrial frequency with the LV frequency or interval time;
LV simulation stimulus threshold;
LV-R wave morphology analysis; and,
QRS far-field analysis (if the FF-QRS morphology remains the same, a dislocation is to be assumed when L-VF is indicated—specifically in the case of atrial fibrillation).

FIG. 6 shows an example of biventricular detection. As shown in FIG. 6, in at least one embodiment, biventricular detection includes counter logic and is represented as a marker chain.

In one or more embodiments, the detection using the tachycardia identification unit may be performed via just one detection counter, which is incremented whenever an interval falls below the programmed tachycardia zone limit. In at least one embodiment, intervals sensed at the right ventricle and at the left ventricle are used to evaluate which ventricle is quicker using a count interval, wherein a right-ventricular interval is only permitted for the counting whenever it is shorter than or equal to the preceding left-ventricular interval, and a left-ventricular interval is only permitted for the counting whenever it is shorter than the preceding right-ventricular interval.

According to at least one embodiment, the detection counter, implemented in the following example by the function cnt(RV), may increment a counter value by 1 whenever it is addressed:

IF $RV(n) \leq LV(n-1)$ THEN $cnt(RV)$; and,

IF $LV(n) < RV(n-1)$ THEN $cnt(RV)$;

In one or more embodiments, only the "quicker" ventricle side is therefore always used for the tachycardia evaluation. As shown in FIG. 6, in at least one embodiment, the interval markers permissible for the tachycardia evaluation are characterized by the following symbol: ↓.

Figure 7:
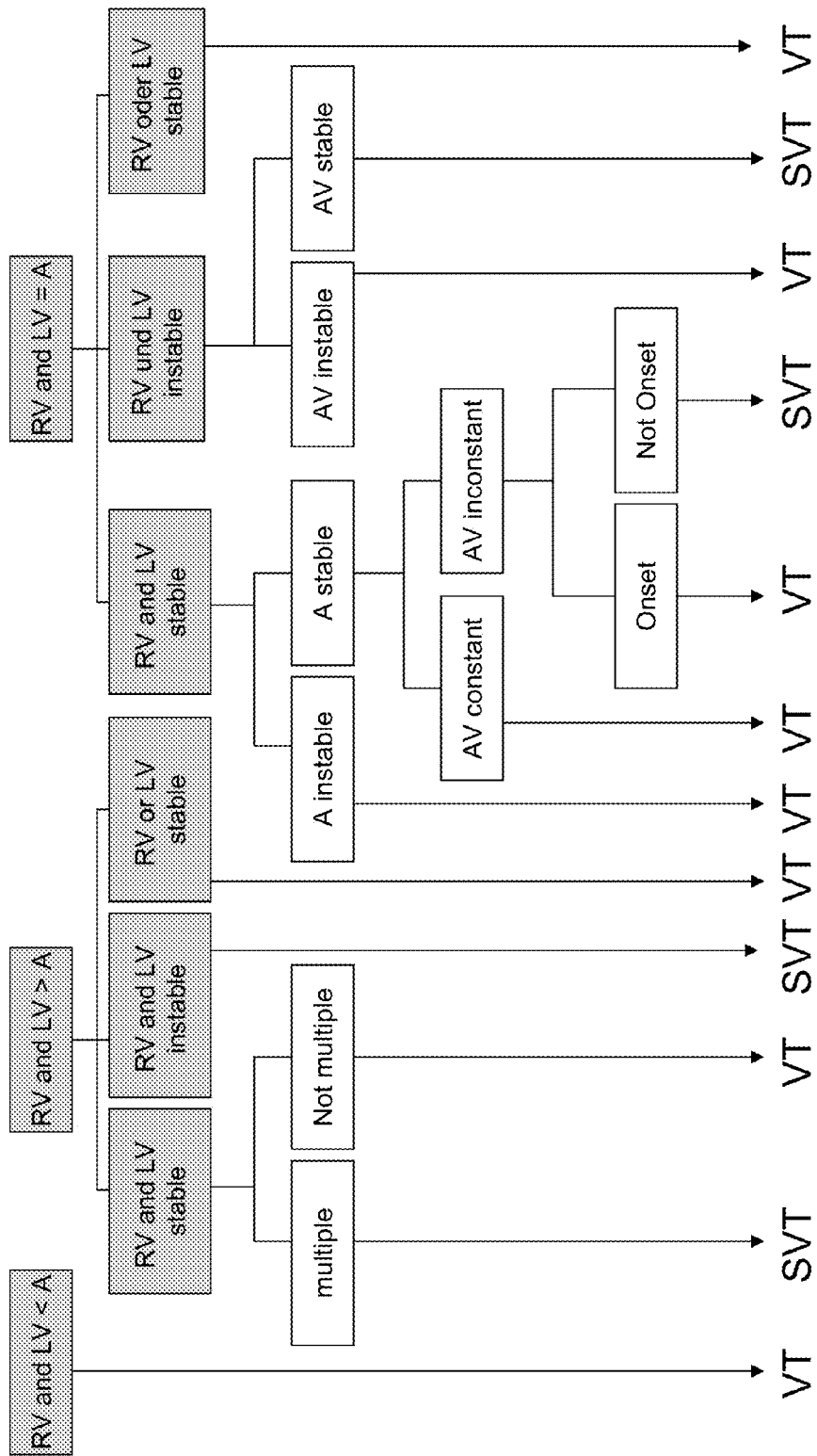
FIG. 7: shows a three-chamber discrimination algorithm.

FIG. 7 shows a three-chamber discrimination algorithm with biventricular detection. According to at least one embodiment, the algorithm as shown in FIG. 7 demonstrates one of the possible implementation variants, since the biventricular discrimination may be integrated into any discrimination algorithms. In one or more embodiments, the sensitivity and specificity of VT/SVT discrimination (the distinction between original ventricular tachycardias (VT) and supraventricular tachycardias (SVT)) may be improved.

According to at least one embodiment, FIG. 7 illustrates the following symbols:
RV: interval time, measured at the right-ventricular electrode;
LV: interval time, measured at the left-ventricular electrode;
A: interval time, measured at the atrial electrode;
AV: atrio-ventricular conductor time (wherein, the algorithm may be extended by a distinction between the right-ventricular and left-ventricular conductor)
VT: evaluation of the current ventricle excitation as the ventricular origin of tachycardia; and,
SVT: evaluation of the current ventricle excitation as the supraventricular origin of tachycardia.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable biventricular heart therapy device comprising:
   a therapy device controller, wherein the therapy device controller comprises
      a tachycardia identification unit connected to a right-ventricular sensing electrode and a left-ventricular sensing electrode;
      wherein said right-ventricular sensing electrode and said left-ventricular sensing electrode are configured to feed at least one signal from a right ventricle of a heart and at least one signal from a left ventricle of the heart, respectively to said tachycardia identification unit;
      wherein said signals represent a course over time of electrical potentials in the heart; wherein the tachycardia identification unit is configured to
         evaluate the signal fed thereto and the course over time thereof,
         generate a tachyarrhythmia signal if the fed signals meet predefined criteria, and,
         identify ventricular tachycardias to simultaneously evaluate the heart rate at the right-ventricular sensing electrode and at the left-ventricular sensing electrode; and,
   a dislocation identification unit connected to the right-ventricular sensing electrode and to the left-ventricular sensing electrode to obtain signals;
      wherein the dislocation identification unit is configured to
         simultaneously evaluate the heart rate at the right-ventricular sensing electrode and the left-ventricular sensing electrode,
         signal a right-ventricular or left-ventricular dislocation, and
         generate a corresponding dislocation signal whenever the dislocation identification unit senses a sudden rise in heart rate at the right-ventricular or left-ventricular sensing electrode without detecting a significant rhythm change at the left-ventricular or the right-ventricular sensing electrode within a predefined time window or adjustable time window or predefined and adjustable time window,
      wherein in an event of a signaled dislocation of the right-ventricular sensing electrode or of the left-ventricular sensing electrode based on said dislocation signal, the therapy device controller is configured to ignore rhythm information of the dislocated right-ventricular or left-ventricular sensing electrode during tachycardia detection.

2. The heart therapy device according to claim 1, wherein following the dislocation signal of the dislocation identification unit, the tachycardia identification unit is further configured to ignore a signal originating from the dislocated right-ventricular or left-ventricular sensing electrode during tachycardia detection.

3. The heart therapy device according to claim 1, further comprising at least one atrial sensing electrode, wherein the dislocation identification unit is further configured to check for the right-ventricular or left-ventricular sensing electrode dislocation when the implantable biventricular heart therapy device senses an atrial fibrillation via the at least one atrial sensing electrode.

4. The heart therapy device according to claim 1, wherein the dislocation identification unit is further configured to signal said left-ventricular dislocation identification using at least one criteria of
   a maximum permissible anteriority of a left-ventricular contraction before a right-ventricular contraction,
   stability of conduction time from an atrium of the heart to the heart's right ventricle,
   a rate comparison between the heart's atrium and the heart's left ventricle,
   a left-ventricular stimulation stimulus threshold, and,
   morphology of left-ventricular R-waves before a detected tachycardia with confirmed amplitudes, impedances and stimulus thresholds.

5. The heart therapy device according to claim 1, further comprising a right-atrial electrode, wherein the implantable biventricular heart therapy device is a three-chamber device connected to the right-atrial electrode, the right-ventricular electrode and the left-ventricular electrode.

6. The heart therapy device according to claim 5, wherein the tachycardia identification unit is further configured to carry out an extended three-chamber discrimination algorithm, in which interval information of the left ventricle and conduction times from the heart's atrium to the heart's left ventricle are recorded and an origin of the tachycardia is classified therefrom.

7. The heart therapy device according to claim 5, wherein the tachycardia identification unit is further configured to
   initially exclusively carry out right-ventricular tachycardia detection until a stable electrode position in the heart's left ventricle is automatically determined, and, then
   automatically activate biventricular detection of the heart's right ventricle and the heart's left ventricle once the stable electrode position in the left ventricle is determined.

8. The heart therapy device according to claim 1, wherein the tachycardia identification unit is further configured to
   evaluate the left-ventricular rhythm,
   discriminate between a physiological rise in heart rate and a suddenly occurring ventricular tachycardia,
   extend a sudden-onset criterion based on the left-ventricular rhythm evaluation, and
   only signal a sinus tachycardia
      when there is no sudden rise in heart rate in the heart's right ventricle and no sudden rise in heart rate in the heart's left ventricle, or interventricular conduction times remain unchanged under consideration of a tolerance, or when there is no sudden rise in heart rate in the heart's right ventricle and no sudden rise in heart rate in the heart's left ventricle, and the interventricular conduction times remain unchanged under consideration of a tolerance.

9. The heart therapy device according to claim 1, wherein the tachycardia identification unit is further configured to
apply a ventricular stability criterion,
distinguish between a stable monomorphic ventricular tachycardia and a conducted atrial fibrillation, wherein a ventricular tachycardia (VT) is only detected when rhythm in both is the heart's left ventricle and the heart's right ventricle are classified as stable.

10. The heart therapy device according to claim 1, further comprising a timer, wherein the therapy device controller is further configured to automatically switch the timer to a control based on signals detected in the left ventricle when the at least one signal from the left ventricle is classified as suitable for the tachycardia detection, and no left-ventricular sensing electrode dislocation is identified.

11. The heart therapy device according to claim 1, wherein the tachycardia identification unit comprises two detection counters, wherein the two detection counters comprise a right ventricle detection counter and a left ventricle detection counter, wherein, when a predefined counter state is reached, one of the right ventricle detection counter and the left ventricle detection counter is configured to trigger a corresponding detection and a corresponding tachyarrhythmia signal.

12. The heart therapy device according to claim 1, wherein the tachycardia identification unit comprises a single detection counter for both the at least one signal from the heart's right ventricle and the at least one signal from the heart's left ventricle, wherein, during a deviating interval time between the at least one signal from the heart's left ventricle and the at least one signal from the heart's right ventricle, the tachycardia detection is determined by evaluating which ventricle of the heart's right ventricle and the heart's left ventricle is quicker using a count interval, wherein the quicker ventricle is the ventricle with a shorter count interval.

13. The heart therapy device according to claim 1, wherein the tachycardia identification unit is further configured to switch between exclusively right-ventricular tachycardia identification and biventricular tachycardia identification of the heart's right ventricle and the heart's left ventricle.

14. The heart therapy device according to claim 1, further comprising a shock electrode configured to deliver at least one defibrillation shock, wherein the therapy device controller is further configured to carry out an additional dislocation check of the left-ventricular sensing electrode after each delivery of said at least one defibrillation shock.

15. The heart therapy device according to claim 1, wherein the dislocation identification unit is further configured to exclusively detect a dislocation of a left-ventricular electrode.

* * * * *